(12) United States Patent
Winzenburg et al.

(10) Patent No.: US 10,722,471 B2
(45) Date of Patent: Jul. 28, 2020

(54) GALENIC FORMULATIONS OF ORGANIC COMPOUNDS

(71) Applicant: Novartis AG, Basel (CH)

(72) Inventors: Gesine Winzenburg, Basel (CH); Bernd Trueby, Basel (CH); Fabian Chen, East Hanover, NJ (US); Surya Prakash Ayalasomayajula, East Hanover, NJ (US); Christopher Bush, East Hanover, NJ (US); Masha Berkhin, East Hanover, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/074,579

(22) PCT Filed: Feb. 2, 2017

(86) PCT No.: PCT/IB2017/050569
§ 371 (c)(1),
(2) Date: Aug. 1, 2018

(87) PCT Pub. No.: WO2017/134597
PCT Pub. Date: Aug. 10, 2017

(65) Prior Publication Data
US 2019/0083406 A1    Mar. 21, 2019

Related U.S. Application Data

(60) Provisional application No. 62/293,005, filed on Feb. 9, 2016.

(30) Foreign Application Priority Data

Feb. 3, 2016 (EP) ..................................... 16154153

(51) Int. Cl.
| | | |
|---|---|---|
| A61K 9/28 | (2006.01) | |
| A61K 31/225 | (2006.01) | |
| A61K 31/41 | (2006.01) | |
| A61K 9/00 | (2006.01) | |
| A61K 9/20 | (2006.01) | |
| A61K 9/48 | (2006.01) | |
| A61P 9/04 | (2006.01) | |
| A61K 31/216 | (2006.01) | |

(52) U.S. Cl.
CPC .............. *A61K 9/28* (2013.01); *A61K 9/0053* (2013.01); *A61K 9/2009* (2013.01); *A61K 9/2013* (2013.01); *A61K 9/2054* (2013.01); *A61K 9/282* (2013.01); *A61K 9/2813* (2013.01); *A61K 9/2846* (2013.01); *A61K 9/4808* (2013.01); *A61K 31/216* (2013.01); *A61K 31/225* (2013.01); *A61K 31/41* (2013.01); *A61P 9/04* (2018.01)

(58) Field of Classification Search
CPC ...... A61K 9/28; A61K 9/0053; A61K 9/2009; A61K 9/2013; A61K 9/2054; A61K 9/2813; A61K 9/282; A61K 9/2846; A61K 9/4808; A61K 31/225; A61K 31/41
See application file for complete search history.

(56) References Cited

U.S. PATENT DOCUMENTS

| | | | |
|---|---|---|---|
| 6,740,341 B1 * | 5/2004 | Holt ..................... | A61K 9/0056 424/490 |
| 8,101,659 B2 | 1/2012 | Ksander et al. | |
| 2010/0267786 A1 * | 10/2010 | Al-Fayoumi ........ | A61K 9/2054 514/381 |
| 2011/0311631 A1 * | 12/2011 | Baer .................... | A61K 9/5078 424/486 |

FOREIGN PATENT DOCUMENTS

| | | |
|---|---|---|
| EP | 1467728 A1 | 10/2004 |
| WO | WO2009/061713 A1 | 5/2009 |

OTHER PUBLICATIONS

Anonymous:, "European Medicines Agency decision P/0106/2014", Jun. 11, 2014, pp. 1-8. Retrieved from the Internet: URL:http://www.ema.europa.eu/docs/en_GB/document_library/PIP_decision/C500168118.pdf [retrieved on Jul. 8, 2016].

Aleksovski et al:, "Mini-tablets: a contemporary system for oral drug delivery in targeted patient groups", Expert Opinion on Drug Delivery, vol. 12, No. 1, Jan. 2, 2015, pp. 65-84.

Center for Drug Evaluation and Research Application No. 207620Orig1s000; https://www.accessdata.fda.gov/drugsatfda_docs/nda/2015/207620Orig1s000ChemR.pdf, 2015.

Gori and Senni, "Sacubitril/valsartan (LCZ696) for the treatment of heart failure", Expert Review of Cardiovascular Therapy, 14(2):145-153, 2016.

* cited by examiner

*Primary Examiner* — Doan T Phan
(74) *Attorney, Agent, or Firm* — Judith D. Kuntz

(57) ABSTRACT

The present invention relates to a solid unit oral dosage form comprising sacubitril and valsartan in a 1:1 molar ratio, preferably in the form of the so-called angiotensin receptor neprilysin inhibitor (ARNI) LCZ696, which is a complex salt hydrate of sacubitril, valsartan, and sodium ions, appropriate for use in pediatrics or other patients where low and individual dosing is required or who encounter problems with swallowing e.g. as a result of a disease or because of age, to the manufacture of said solid dosage form and to invention embodiments relating to therapy using said dosage form.

18 Claims, No Drawings

GALENIC FORMULATIONS OF ORGANIC COMPOUNDS

FIELD OF THE INVENTION

The present invention relates to a solid unit oral dosage form comprising sacubitril and valsartan in a 1:1 molar ratio, preferably in the form of the so-called angiotensin receptor neprilysin inhibitor (ARNI) LCZ696, which is a complex salt hydrate of sacubitril, valsartan, and sodium ions, appropriate for use in pediatrics or other patients where low and individual dosing is required or who encounter problems with swallowing e.g. as a result of a disease or because of age, to the manufacture of said solid dosage form and to invention embodiments relating to therapy using said dosage form.

BACKGROUND OF THE INVENTION

LCZ696: The NEP inhibitor prodrug sacubitril (AHU377, (2R,4S)-5-biphenyl-4-yl-4-(3-carboxy-propionylamino)-2-methyl-pentanoic acid ethyl ester, also named N-(3-carboxyl-1-oxopropyl)-(4S)-(p-phenylphenylmethyl)-4-amino-(2R)-methyl butanoic acid ethyl ester; IUPAC name 4-{[(1S,3R)-1-([1,1'-biphenyl]-4-ylmethyl)-4-ethoxy-3-methyl-4-oxobutyl]amino}-4-oxobutanoic acid) together with valsartan, a known angiotensin receptor blocker (ARB), forms a sodium salt hydrate complex, known as LCZ696, comprising the anionic forms of sacubitril and valsartan, sodium cations and water molecules in the molar ratio of 1:1:3:2.5, respectively (ratio of 6:6:18:15 in the asymmetric unit cell of the solid state crystal), and which is schematically present in the following formula:

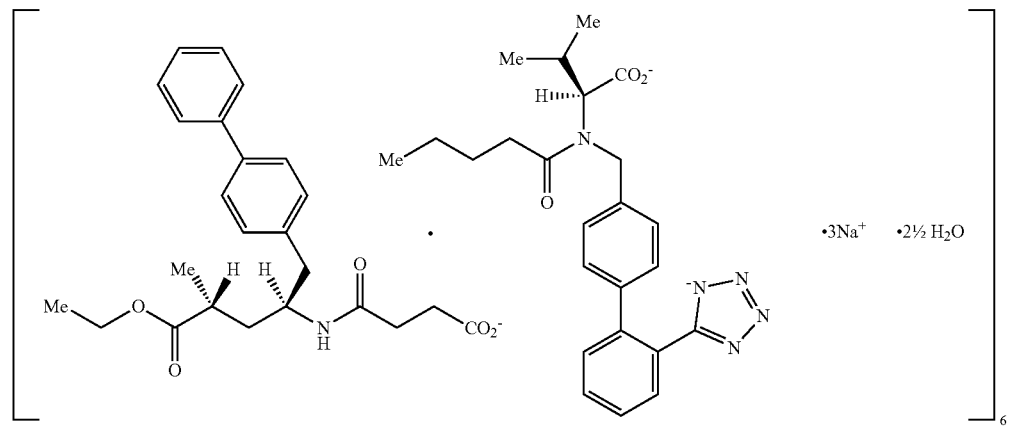

Said complex is also referred to by the following chemical names: Trisodium [3-((1S,3R)-1-biphenyl-4-ylmethyl-3-ethoxycarbonyl-1-butylcarbamoyl)propionate-(S)-3'-methyl-2'-(pentanoyl {2''-(tetrazol-5-ylate)biphenyl-4'-ylmethyl}amino)butyrate]hemi-pentahydrate or Octadecasodium hexakis(4-{[(1S,3R)-1-([1,1'-biphenyl]-4-ylmethyl)-4-ethoxy-3-methyl-4-oxobutyl]amino}-4-oxobutanoate) hexakis(N-pentanoyl-N-{[2'-(1H-tetrazol-1-id-5-yl)[1,1'-biphenyl]-4-yl]methyl}-L-valinate)—water (1/15) (IUPAC nomenclature).

Ingestion of LCZ696 results in systemic exposure to sacubitril, the neprilysin (neutral endopeptidase 24.11, NEP) inhibitor (NEPi) prodrug which is converted to the active form LBQ657 (2R,4S)-5-biphenyl-4-yl-4-(3-carboxy-propionyl amino)-2-methyl-pentanoic acid), and valsartan providing inhibition of the angiotensin II type 1 (AT1) receptor, in a 1:1 molar ratio.

Combinations of sacubitril and valsartan, and in particular LCZ696 and formulations thereof, have been previously disclosed in WO 2003/059345, WO 2007/056546, and WO 2009/061713, which are herein incorporated by reference.

Mode of action: Neprilysin inhibition leads to enhanced levels of the physiologically active natriuretic peptides (NPs), including atrial natriuretic peptide (ANP). NPs mediate their cardiovascular effects through activation of the natriuretic peptide receptor A (NPR-A) and their second messenger cyclic GMP (cGMP), resulting in potent vasodilation, natriuresis, diuresis, inhibition of the renin angiotensin aldosterone system (RAAS) by reducing renin and aldosterone release, reduced sympathetic drive, and antiproliferative and antihypertrophic effects on vascular endothelium and smooth muscle cells. The angiotensin receptor blocker (ARB) component provides AT1 receptor antagonism, preventing the deleterious effects of angiotensin II and thereby lowering peripheral vascular resistance. By delivering dual and potentially complementary beneficial effects, LCZ696 may offer clinical benefits to patients with cardiovascular and renal disease.

Various uses of combinations of sacubitril and valsartan, and in particular LCZ696, for the treatment of patients with various cardiovascular and/or renal diseases have been described in e.g. WO 2003/059345, WO 2007/056546, WO 2012/027237, WO 2014/029848, WO 2015/030711, and WO 2015/028941.

In particular, neprilysin (NEP) inhibition with chronic oral administration of LCZ696 can promote the endogenous capacity of the body to compensate for Heart Failure (HF) exacerbations by potentiating the activity of natriuretic peptides secreted by the heart in response to cardiac stress and increased intravascular volume. LCZ696, unlike any other therapy for HF, provides concomitant inhibition of NEP and the angiotensin type 1 (AT1) receptor. The resulting increase in natriuretic peptide (NP) activity due to NEP inhibition and AT1 receptor blockade through renin-angiotensin-aldosterone system (RAAS) inhibition have complementary effects on the cardiovascular (CV) system that benefit HF patients.

In PARADIGM-HF (CLCZ696B2314; N=8442), the pivotal Phase 3 study in adult patients with HF with reduced ejection fraction (HFrEF), LCZ696 was superior to enalapril (the standard of care) in delaying time to first occurrence of composite endpoint of CV death or HF hospitalization, with a 20% relative risk reduction (RRR) (p=0.0000002). In addition, LCZ696 was superior to enalapril in delaying time to CV death with a 20% RRR p=0.00004) and in delaying time to first HF hospitalization with 21% RRR (p=0.00004). PARADIGM-HF also showed that LCZ696 is generally safe and well tolerated in adult patients with HF (McMurray et al, 2014).

LCZ696 is now considered for use in children as an alternative to currently available therapies for cardiovascular diseases such as heart failure (HF).

Congenital heart disease and cardiomyopathy are the two most common causes of pediatric HF. An incidence of 10.4% has been reported in HF patients <16 years with congenital or acquired heart disease and a 2 to 7.7/100,000 incidence of HF in the general pediatric population. The highest incidence of HF occurs in infants and children between 0 and 4 years of age. A second peak of pediatric HF, due mainly to cardiomyopathy and unrepairable or palliative repair of congenital heart defects causes, appears between ages 10 and 18. It is estimated that between 12,000 to 35,000 children below age 19 are diagnosed with pediatric HF in the United States each year. The largest HF burden comes from children born with congenital malformations. Congenital heart disease occurs in approximately 8 per 1,000 live births of which 1-2 per 1,000 develop HF. A wide variety of congenital abnormalities may be present. Most of these children are diagnosed before age 1 and many have early surgical intervention, usually before age 2.

The other main cause of pediatric HF is cardiomyopathy. At any given time point, cardiomyopathies affect at least 100,000 children worldwide. Recent studies indicate that the annual incidence of cardiomyopathy in the US, Australia, United Kingdom and Ireland are similar at approximately 1 per 100,000 children aged 18 or younger. The highest incidence is in children under 1 year of age. Dilated cardiomyopathy (usually diagnosed as idiopathic, familial, or myocarditis) is the most common type. In the United States, the annual incidence of dilated cardiomyopathy in children younger than 18 years is approximately 0.57 cases per 100,000 person-years. Hypertrophic cardiomyopathy due to familial isolated cardiomyopathy, an inborn error of metabolism, or a malformation syndrome is the next most common type. Cardiomyopathy can also be associated with muscular dystrophies such as Duchenne's muscular dystrophy and myotonic dystrophy. Other types of cardiomyopathy, including restrictive and arrhythmic cardiomyopathies are rarer. In 41-63% of the cardiomyopathy cases, the diagnosis was made during the first year of life, usually due to symptoms of HF. Morbidity and mortality of these diseases are high, and they are the most common cause of a heart transplant in children older than 1 year. Nearly 40% of children with a symptomatic cardiomyopathy either undergo heart transplantation or die within 2 years.

Remarkably, no trial with other drugs to date has demonstrated an outcome benefit of any pharmacotherapy in children with HF. In order to study the efficacy and safety of LCZ696 in children, there is a need for appropriate formulations in order to allow for pediatric studies and later pediatric treatment. Such formulations suitable for pediatric patients might also be suitable for other patients encountering problems with swallowing e.g. as a result of a disease or because of age or for psychological reasons, Liquid dosage forms would allow for such individualized and easy to swallow delivery to patients—however, the chemical and physical stability and thus storage and transport of LCZ696 as mentioned, in particular the stability of the complex and especially of the prodrug sacubitril, may be hampered in liquids, the excipient tolerability may cause limitations, and taste considerations may make it difficult to supply drugs in dissolved or dispersed form in liquid formulations.

Normal solid oral dosage forms, that is, tablets and capsules for adults patients and/or patients where the standard adult dosage is to be administered, on the other hand, allow for less swallowability and dosing flexibility.

Small particle solid dosage forms, like powders, granules, agglomerates or pellets (e.g. resulting from fluid bed or other manufacturing processes), small capsules or uncoated tablets, would in principle allow to meet the dosage flexibility requirements—however, taste masking issue considerations apply to most of these variants, and it may be difficult to implement them if administration together with food is considered which allows to make the ingestion of the drugs more attractive and palatable for children and other patients.

LCZ696 as currently marketed (Tradename ENTRESTO™) is available in an oral dosage form as immediate release film-coated tablets of 200, 100 and 50 mg. This formulation does not fulfill the requirements of a pediatric formulation in terms of strength, dosing flexibility, patient acceptability (e.g. swallow ability) and size.

Also the physical-chemical properties, especially the stability of the prodrug sacubitril, and to a smaller extent the taste of the drug substance precludes the development of a liquid oral formulation which is standard of care for children.

A dosage form sometimes considered for pediatric use are formulations in form of minitablets, which may be provided with or without small amount of soft food, e.g. pudding or apple sauce. However, due to the very small size of these tablets of a few mg, the tablet manufacturing process with uniformity of content at the individual mini-tablet level such as that described in WO 2010/086312 can be extremely difficult. Further, not all of the pharmacopoeia methods established for pharmaceuticals are applicable for minitablets. So far mini-tablets are not described in any pharmacopoeial monographs.

In addition, due to the chemical nature of LCZ696 as a salt complex a premature release and dissolution of the drug when mixed with food should be prevented, whilst still allowing an immediate release profile upon ingestion.

In particular, the release profile of a pediatric formulation—in the appropriate overall dosage—should also show bioequivalence to the already available film tablets of LCZ696 in dosage strengths of 50 mg, 100 mg and 200 mg.

It is, therefore, an unmet need to develop and provide a pediatric formulation of LCZ696 that addresses the deficiencies of the marketed film-coated tablet in terms of a pediatric application, whereby said formulation has the size, dosing flexibility, acceptance and palatability desirable for an application in children and other patients as mentioned above while maintaining bioavailability comparable to the marketed drug product.

SUMMARY OF THE INVENTION

In spite of the technical difficulties and the formulation constraints of LCZ696, surprisingly already known technically demanding state of the art technology, especially with suitable process adaptations, could be used and was developed within the scope of the present invention in the production of minitablets, which made it possible to overcome the issues and to provide a solid unit dosage form of a 1:1 molar ration of sacubitril and valsartan for oral administration in form of a minitablet having a core and an outer coating, wherein:

the core of said tablet comprises as active ingredient a therapeutically effective amount of sacubitril and valsartan in a 1:1 molar ratio, preferably in the form of LCZ696; and at least one pharmaceutically acceptable excipient, and the outer coating is in form of a controlled release and/or a protective film-coating, which optionally also has taste masking properties, in particular the film-coating has a controlled release functionality with regard to food to be admixed before administration.

In one embodiment, the effective amount of the active ingredient is between about 2 mg and about 5 mg per minitablet, corresponding to the respective combined amount of valsartan (free acid) and sacubitril (free acid) in a 1:1 molar ratio.

In another embodiment, said minitablet has a size of between 1 mm and 4 mm.

Accordingly, in one aspect, the present invention relates to a solid unit dosage form for oral administration in form of a minitablet having a core and an outer coating, wherein the core comprises as active ingredient a therapeutically effective amount of sacubitril and valsartan in a 1:1 molar ratio; and at least one pharmaceutically acceptable excipient, wherein the effective amount of the active ingredient is between about 2 mg and about 5 mg per minitablet, corresponding to the respective combined amount of valsartan (free acid) and sacubitril (free acid) in a 1:1 molar ratio, the outer coating is in form of a controlled release and/or a protective film-coating, and said minitablet has a size of between 1 mm and 4 mm.

In one embodiment, the active ingredient is provided in the form of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate (LCZ696) as described in more detail above in the introduction section.

In one aspect, said minitablets are provided together with a dispenser for ease of dosing and administration.

In one aspect, said minitablets are provided in a container such as a capsule. Such a capsule contains a defined number of minitablets according to the invention. Said number can be selected from 1, 2, 3, 4, 5, 6, 7, 8, 9, 10, 11, 12, 13, 14, 15, 16, 17, 18, 19, and 20; preferably the container, preferably the capsule, contains 4 or 10 minitablets.

In one aspect, the present invention also relates to a process for manufacturing the solid oral dosage form as described herein.

In another aspect, the present invention provides a solid unit dosage form of sacubitril and valsartan in a 1:1 molar ratio, in particular in the form of LCZ696, for oral administration in form of coated minitablets for use as an age-appropriate pediatric formulation, meeting the technical, administration and pharmacokinetic requirements.

In another aspect, the present invention provides a solid unit dosage form of sacubitril and valsartan in a 1:1 molar ratio for oral administration in the form of a minitablet as described herein for use in the treatment of a disease or condition in a pediatric population, in particular for use in the treatment of heart failure in a patient belonging to a pediatric population.

However, the use of the solid unit dosage form according to the present invention is not restricted to an application in children but can generally be used, for example, in patients with difficulties in swallowing due to a disease or age of the patient or due to psychological restraints limiting the ability to orally ingest the marketed tablets of LCZ696. Accordingly, in further aspect, the present invention relates to the use of a solid oral dosage form as described herein in the treatment or prevention of chronic heart failure, hypertension, angina, myocardial infarction, atherosclerosis, diabetic nephropathy, diabetic cardiac myopathy, renal insufficiency, peripheral vascular disease, left ventricular hypertrophy, cognitive dysfunction, and stroke, in particular in patients where low and individual dosing is required or who encounter problems with swallowing.

Further features and advantages of the disclosure will become apparent from the following detailed description of the invention.

DETAILED DESCRIPTION OF THE INVENTION

Definitions:

Throughout this specification and in the claims that follow, the following terms are defined with the following meanings, unless explicitly stated otherwise. The following definitions may be used independently to provide more specific versions of one or more or (as far as present) all generic terms used above or below, thus defining more specific invention embodiments:

The term "prevention" refers to prophylactic administration to a healthy subject to prevent the development of the conditions mentioned herein. Moreover, the term "prevention" means prophylactic administration to patients being in a pre-stage of the conditions to be treated.

The term "treatment" is understood the management and care of a patient for the purpose of combating the disease, condition or disorder.

The terms "effective amount" or "therapeutically effective amount" refer to an amount of a drug or a therapeutic agent that will elicit the desired biological and/or medical response of a tissue, system or an animal (including man) that is being sought by a researcher or clinician. In particular, the terms "effective amount" or "therapeutically effective amount" refer to the amount of the active ingredient or agent which halts or reduces the progress of the condition being treated or which otherwise completely or partly cures or acts palliatively on the condition, e.g. chronic heart failure.

The terms "patient" include, but are not limited to, humans, dogs, cats, horses, pigs, cows, monkeys, rabbits and mice. The preferred patients are humans.

The terms "administration of" and or "administering a" compound should be understood to mean providing a compound of the invention or a pharmaceutically acceptable salt or ester thereof, or a pro-drug thereof to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "about" as used herein refers to +/−20%, +/−10%, +/−5% or +/−2% of a value.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The term "release" as used herein refers to a process by which the pharmaceutical oral dosage form is brought into contact with a fluid and the fluid transports the drug(s) outside the dosage form into the fluid that surrounds the dosage form. The combination of delivery rate and delivery duration exhibited by a given dosage form in a patient can be described as its in vivo release profile. The release profiles of dosage forms may exhibit different rates and durations of release and may be continuous. Continuous release profiles include release profiles in which one or more active ingredients are released continuously, either at a constant or variable rate.

For the purposes of the present application, an immediate release formulation is a formulation showing a release of the active substance(s), which is not deliberately modified by a special formulation design or manufacturing method.

For the purposes of the present application, a "controlled release formulation" is a formulation showing a release of the active substance(s), which is deliberately controlled (modified) by a special formulation design or manufacturing method. This controlled release can be typically obtained by delaying the time of release of the active ingredient. Typically for the purposes of the present invention, a controlled release refers to a release delayed by 30-60 mins.

The term "disintegration" as used herein refers to a process where the pharmaceutical oral dosage form, typically by means of a fluid, falls apart into separate particles and is dispersed. Disintegration is achieved when the solid oral dosage form is in a state in which any residue of the solid oral dosage form, except fragments of insoluble coating or capsule shell, if present, remaining on the screen of the test apparatus is a soft mass having no palpably firm core in accordance with USP<701>. The fluid for determining the disintegration property is water, such as tap water or deionized water. The disintegration time is measured by standard methods known to the person skilled in the art, see the harmonized procedure set forth in the pharmacopeias USP <701> and EP 2.9.1 and JP.

The term "dissolution" or "dissolve" as used herein refers to a process by which a solid substance, here especially the active ingredient, is dispersed in molecular form in a medium, leading to a clear solution if no other opaque materials are present. The dissolution rate of the active ingredient of the pharmaceutical oral dosage form of the invention is defined by the amount of drug substance (measured as sacubitril and/or valsartan individually or together in the context of the present invention) that goes in solution per unit time under standardized conditions of liquid/solid interface, temperature and solvent composition. The dissolution rate is measured by standard methods known to the person skilled in the art, see the harmonized procedure set forth in the pharmacopeias USP <711> and EP 2.9.3 and JP. For the purposes of this invention, the test for measuring the dissolution of the individual active ingredient is performed following pharmacopeia USP <711> at pH 6.8 using a paddle stirring element at 50 rpm (rotations per minute). The dissolution medium is preferably a buffer, typically a pH 6.8 phosphate buffer, e.g. 900 mL of 0.05M phosphate buffer at pH 6.8. Alternatively, the test is for measuring the dissolution of the individual active ingredient is performed following pharmacopeia USP <711> at pH 2.0 using a paddle method at 50 rpm (rotations per minute). The dissolution medium typically is 900 mL of 0.01 N HCl at pH 2.0 and 37±0.5° C., but it can also be a buffer, typically a phosphate buffer, especially with a molarity of 0.1 M at pH 2.0 and 37±0.5° C. Alternatively, the test is for measuring the dissolution of the individual active ingredient is performed following pharmacopeia USP <711> at pH 4.5 using a paddle stirring element at 50 rpm or 75 rpm as specified. The dissolution medium is preferably a buffer, typically a phosphate buffer (e.g. 900 ml or 1000 mL of pH 4.5 phosphate buffer). All dissolution testing is carried out at the indicated temperature, in particular at 37±0.5° C.

The term "minitablets" within the scope of this application denotes small tablets with an overall weight of approximately 2 to 30 mg, e.g. approximately 4 to 9 mg, e.g.

approximately 7 mg, in their uncoated form, and approximately 2.2 to 32 mg, e.g. approximately 4.1 to 10 mg, e.g. approximately 7.1 to 7.5 mg in their coated form.

Minitablets are a specific form of multiparticulates as defined herein. They can be prepared as described herein, including preparation from other, smaller multiparticulates, such as particles, granules or beads. The minitablets may have any shape known to the skilled person for tablets, e.g. round e.g. with a diameter of about 1.25 to 3 mm or as defined elsewhere herein; cylindrical e.g. having a convex upper face and convex lower face and e.g. with a cylindrical diameter and height independently of each other are from 1 to 3 mm or as defined elsewhere herein; or biconvex minitablets e.g. whose height and diameter are approximately equal and are from 1.25 to 3 mm, or as defined elsewhere herein.

The term "sacubitril and valsartan in a 1:1 molar ratio" as used herein refers to a combination comprising a therapeutically effective amount of a 1:1 molar ratio of (i) valsartan or a pharmaceutically acceptable salt thereof; and (ii) sacubitril or a pharmaceutically acceptable salt thereof, in particular in the form of the combined sodium salt complex trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate (LCZ696), and as defined in more detail below. The term "sacubitril and valsartan in a 1:1 molar ratio" can also refer to alternative complexes or compounds comprising valsartan and sacubitril and linking them together via non-covalent or covalent bonding, optionally via a linker.

Embodiments

Size and Form: In one embodiment of the invention, a solid unit dosage form in the form of a minitablet as described herein above is provided, wherein said minitablet has a diameter of from 1 mm to 3 mm, particularly from 1.25 mm to 2.75 mm, but particularly from 1.5 mm to 2.5 mm. Preferably, the minitablet has a round-curved shape. In one embodiment of the invention, the minitablet has a diameter of 1.9 to 2.1 mm, in particular around 2 mm.

The thickness of the minitablet may, for example, be in the range of from 1 to 3 mm, particularly from 1.5 to 2.6 mm, and particularly from 1.9 to 2.3 mm, in particular around 2 to 2.2 mm.

Active ingredient: In the context of the present invention, the term "sacubitril and valsartan in a 1:1 molar ratio" refers to a combination comprising a therapeutically effective amount of a 1:1 molar ratio of
 (i) valsartan or a pharmaceutically acceptable salt thereof; and
 (ii) sacubitril or a pharmaceutically acceptable salt thereof.

Sacubitril is the INN for N-(3-carboxy-1-oxopropyl)-(4S)-(p-phenylphenylmethyl)-4-amino-2R-methylbutanoic acid ethyl ester. This is a prodrug for (2R,4S)-5-biphenyl-4-yl-4-(3-carboxy-propionyl amino)-2-methyl-pentanoic acid. Sacubitril can be prepared by known methods such as described in U.S. Pat. No. 5,217,996 which is herein incorporated by reference.

Valsartan is S—N-valeryl-N-{[2'-(1H-tetrazole-5-yl)-biphenyl-4-yl]-methyl}-valine. Valsartan or (S)—N-valeryl-N-{[2'-(1H-tetrazole-5-yl)-biphenyl-4-yl]-methyl}-valine) or a pharmaceutically acceptable salt thereof that can be purchased from commercial sources or can be prepared according to known methods, such as described in U.S. Pat. No. 5,399,578 and EP 0443983, whose preparative teachings are incorporated by reference herein. Valsartan may be used in certain embodiments of the invention in its free acid form, as well as in any suitable salt form. Depending upon the circumstance, esters or other derivatives of the carboxylic grouping may be employed as well as salts and derivatives of the tetrazole grouping.

In one embodiment thereof, the combination comprises a 1:1 molar ratio
 (i) of valsartan; and
 (ii) of sacubitril or a pharmaceutically acceptable salt thereof, such as sodium or calcium salt.

In another embodiment thereof, said combination is provided in the form of a compound of the formula (I)

$$[(A_1)(A_2)](Na^+)_y \cdot xH_2O \qquad (I)$$

wherein
A$_1$ is valsartan in the anionic form;
A$_2$ is sacubitril in the anionic form;
Na$^+$ is a sodium ion;
y is 1 to 3, preferably 1, 2, or 3; and
x is 0 to 3, preferably 0, 0.5, 1, 1.5, 2, 2.5, or 3.

In one embodiment, y is 3 and x is 2.5.

In particular, the compound is trisodium [3-(1S,3R)-1-biphenyl-4-ylmethyl-3-ethoxycarbonyl-1-butylcarbamoyl) propionate-(S)-3'-methyl-2'-(pentanoyl {2''-(tetrazol-5-ylate)biphenyl-4'-ylmethyl}amino)butyrate] hemipentahydrate (LCZ696).

In a preferred embodiment, the compound trisodium [3-((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate) biphenyl-4'-ylmethyl}amino)butyrate] hemipentahydrate is present in crystalline form.

The corresponding active ingredient or a pharmaceutically acceptable salt thereof may also be used in the form of a hydrate or include other solvents used for crystallization.

Preferably, the compounds sacubitril or a salt thereof, valsartan or a salt thereof, or LCZ696 are substantially pure or in a substantially pure form. As used herein, "substantially pure" refers to at least about 90% purity, more preferably at least about 95% and most preferably at least about 98% purity.

Also preferred is that these compounds are solid or a solid form or solid state. The solid, solid form or solid state can be crystalline, partially crystalline, amorphous or polyamorphous, preferably in the crystalline form.

Amount of active ingredient: In one embodiment of the invention, a solid unit dosage form in form of a minitablet as described herein above is provided, wherein said minitablet contains an effective amount of the active ingredient is between about 2 mg and about 5 mg per minitablet, particularly from about between 2.5 mg and 4.0 mg per minitablet, corresponding to the respective combined amount of valsartan (free acid) and sacubitril (free acid) in a 1:1 molar ratio. In one preferred embodiment, each minitablet contains an amount of 3.125 mg active ingredient per tablet as just defined.

In one embodiment, the active ingredient is provided in the form of LCZ696. The effective amount of LCZ696 is based on the weight of the two active ingredients sacubitril and valsartan without the weight of the sodium and bound water comprised in the complex; i.e. the effective amount from LCZ696 in the minitablets ranges from about between 2 mg to about 5 mg LCZ696 per unit dosage form, particularly from about between 2.5 mg and 4.0 mg per unit dosage form. In one embodiment of the invention, each minitablet contains an amount as just defined of 3.125 mg LCZ696. Taking the sodium and hydrate water into account, said mini-tablets contain between about 3 mg to about 4 mg, preferably about 3.534 mg, trisodium [3-((1S,3R)-1-biphenyl-4-ylmethyl-3-ethoxycarbonyl-1-butylcarbamoyl) propionate-(S)-3'-methyl-2'-(pentanoyl {2''-(tetrazol-5-ylate)biphenyl-4'-ylmethyl}amino)butyrate] hemipentahydrate per tablet.

Core: The core of the minitablet according to the invention comprises at least one pharmaceutically acceptable excipient. Such excipients (or additives) are suitable for the preparation of the solid oral dosage form according to the present invention. Tabletting aids, commonly used in tablet formulation can be used and reference is made to the extensive literature on the subject, see in particular Fiedler's "Lexikon der Hilfstoffe," 4th Edition, ECV Aulendorf 1996, which is incorporated herein by reference. These include, but are not limited to, fillers or diluents, binders, lubricants, glidants, stabilizing agents, surfactants, softeners, pigments and the like.

In one embodiment, the present invention relates to a solid oral dosage form comprising a therapeutically effective amount of sacubitril and valsartan in a 1:1 molar ratio, in particular in the form of LCZ696, and at least a filler (diluent) as an additive. Further additives include, but are not limited to one or more selected from the group consisting of binders, lubricants, glidants (antitacking agents), stabilizing agents, surfactants, pigments, softeners and the like. The amounts of the active ingredient and further additives are preferably those as defined below.

In another embodiment, the present invention relates to a solid oral dosage form comprising a therapeutically effective amount of sacubitril and valsartan in a 1:1 molar ratio, in particular in the form of LCZ696, and a filler (diluent) and a binder as additives. Further optional additives include, but are not limited to, a lubricant and one or more, e.g. two, glidants, and optionally one or more stabilizing agents, surfactants, pigments and softeners and the like. The amounts of the active ingredient and further additives are preferably those as defined herein below.

In a further embodiment, the present invention relates to a solid oral dosage form comprising a therapeutically effective amount of sacubitril and valsartan in a 1:1 molar ratio, in particular in the form of LCZ696, and a filler (diluent), a binder, a lubricant and one or more, e.g. two, glidants as additives. Further optional additives include, but are not limited to, one or more stabilizing agents, surfactants, pigments and softeners and the like. The amounts of the active ingredient and further additives are preferably those as defined herein below.

One or more of these additives can be selected and used by a person skilled in the art having regard to the particular desired properties of the solid oral dosage form by routine experimentation and without any undue burden.

A filler or diluent may be selected from customary additives known in the art, such as, for example, microcrystalline cellulose (cellulose MK GR), confectioner's sugar, compressible sugar, dextrates, dextrin, dextrose, lactose, in particular anhydrous lactose, mannitol, starches, e.g., potato starch, wheat starch, and corn starch; powdered cellulose, sorbitol, sucrose, and microcrystalline cellulose; preferably the filler is a microcrystalline cellulose, e.g., products available under the registered trade marks AVICEL, FILTRAK, HEWETEN or PHARMACEL. A most preferred filler is microcrystalline cellulose, in particular a microcrystalline cellulose having a density of about 0.45 g/cm$^3$, e.g., AVICEL. The filler, in particular the microcrystalline cellulose, may be present in a concentration from about 20% to about 60%; e.g. from about 30% to about 50% by weight of the core (prior to coating), preferably around 40% by weight of the core.

A binder may be selected from customary additives known in the art, such as, for example, cellulose derivatives, in particular hydroxypropyl cellulose (HPC), in particular hydroxylpropylmethyl cellulose having a Brookfield viscosity in the range from 100 to 5000 CPS, e.g. hydroxypropylcellulose (HP cellulose) having a viscosity in the range from 300 to 600 CPS. The binder, in particular the HP cellulose, may be present in a concentration from about 1 to about 40%, from about 2% to about 20%, from 3% to about 10%, in particular from about 3.5% to about 5.5%, especially from about 4% to about 5% by weight of the core (prior to coating). Although some of the excipients could also be considered as disintgrants, for the purposes of the present invention they are preferably regarded as binders.

As lubricants one can mention stearic acid and salts thereof, in particular Magnesium (Mg) stearate, aluminum (Al) or Calcium (Ca) stearate; glycerol esters, in particular PEG 4000 to 8000; hydrogenated castor oil, Na-stearylfumarate, hydrogenated cotton seed oil and others. A most preferred lubricant is Mg stearate and/or stearic acid. The amount of lubricant present may vary within a range of from 0.2 to 6% by weight, in particular, for Mg stearate from 1.0% to 5.0% by weight, e.g., from 1.5% to 3.5%, in particular 2.0% to 3.0% by weight of the core (prior to coating).

As glidants one can mention in particular colloidal silica, such as colloidal silicon dioxide, e.g., AEROSIL, magnesium (Mg) trisilicate, powdered cellulose, starch, talc and tribasic calcium phosphate or combinations thereof. In particular glidants can be contained in the form of combinations of these glidants with fillers or binders, e.g., silicified microcrystalline cellulose (PROSOLV). A most preferred glidant is colloidal silicon dioxide (e.g. AEROSIL 200) and/or talc. AEROSIL® is a trademark from Evonik Industries AG, Darmstadt, Germany. The amount of glidant(s) present may vary within a range of from 0.1 to 5% by weight, e.g. from 1.5 to 3.5% by weight, in particular, for talc from 0.5% to 1.0% by weight and for colloidal silicon dioxide, from 0.2% to 4.0%, in particular 1.0% to 2.0% by weight of the core (prior to coating).

Hence, in one embodiment the solid oral dosage form according to the present invention comprises as an additive a filler, particularly microcrystalline cellulose, and a binder, in particular hydroxypropyl cellulose (HP cellulose).

In one embodiment the solid oral dosage form according to the present invention comprises as an additive, in addition to a filler, a binder and a lubricant, particularly microcrystalline cellulose, hydroxypropyl cellulose and magnesium stearate.

In one embodiment the solid oral dosage form according to the present invention comprises as an additive, in addition to a filler, a binder and a lubricant, at least one glidant, particularly microcrystalline cellulose, hydroxypropyl cellulose, magnesium stearate, and colloidal silicon dioxide and/or talc.

It is a characteristic of the present solid oral dosage forms that they contain only a relatively small amount of excipients given a desired high content of the active ingredient. This challenges the production of physically small unit dosage forms. The total amount of additives in a given uncoated unit dosage (i.e. the core) may be about 70% or less by weight based on the total weight of the core prior to coating, more particularly about 60% or less. Preferably, the excipient content is in the range of about 40% to 59% by weight, more particularly, the excipient content ranges from about 45% to about 54% by weight based on the weight of the core prior to coating. With respect to the total weight of the solid oral dosage form (including core and coating), the total amount of additives of the core may be about 65% or less by weight based on the total weight of the solid oral dosage form, more particularly about 60% or less. Preferably, the additive content is in the range of about 40% to 55% by weight, more particularly, the additive content ranges from about 55% to about 50% by weight based on the weight of the total unit dosage form.

Accordingly, the active ingredient is present in a concentration from 30% to 70%, preferably 40% to 60%, more preferably around 50% by weight of the core prior to any coating.

A preferred amount of a filler in the tablet core, especially of microcrystalline cellulose, ranges from about 35% to 45% by weight, e.g. from 39% to 41% by weight based on the weight of the core prior to coating, respectively.

A preferred amount of a binder in the tablet core, especially of hydroxypropyl cellulose, ranges from 2% to 8% by weight, e.g. from 3.5% to 5.5% by weight, e.g. from 4% to 5% by weight, based on the weight of the core prior to coating, respectively.

A preferred amount of a lubricant in the tablet core, especially of Mg stearate, ranges from 0.2% to 6.0% by weight, e.g. from 1.0% to 5.0% by weight, e.g. from 1.5% to 3.5%, in particular 2.0% to 3.0% by weight of the core prior to coating, respectively.

A preferred amount of a glidant in the tablet core, especially of colloidal silicon dioxide and/or talc, ranges from 0.1% to 5.0% by weight for overall glidant content, e.g. from 1.5% to 3.5%, e.g. from 1.5% to 2.5% by weight of the of the core prior to coating, respectively. In particular, the amount of the individual glidant present ranges for talc from 0.5% to 1.0% by weight and for colloidal silicon dioxide, from 0.2% to 4.0%, e.g. from 1.0% to 2.0% by weight of the core (prior to coating).

In one embodiment, the solid oral dosage according to the invention comprises as excipients microcrystalline cellulose in an amount of 35% to 45% by weight, hydroxypropylcellulose in an amount of 2% to 8% by weight, e.g. from 3.5% to 5.5% by weight, Mg stearate in an amount of 1.0 to 5.0% by weight, e.g. from 1.5% to 3.5% by weight, colloidal silicon dioxide in an amount of from 0.2% to 4.0%, e.g. from 1.0% to 2.0% by weight, and talc in an amount of from 0.5 to 1.0% by weight, wherein the % by weight refers to the % by weight of the core prior to coating.

In one embodiment thereof, the solid oral dosage according to the invention comprises as excipients microcrystalline cellulose in an amount of 35% to 45% by weight, hydroxypropylcellulose in an amount of 2% to 8% by weight, Mg stearate is present in an amount of 1.0 to 5.0% by weight, colloidal silicon dioxide is present in an amount of from 0.2% to 4.0% by weight, and talc is present in an amount of from 0.5 to 1.0% by weight, wherein the % by weight refers to the % by weight of the core prior to coating.

In another embodiment thereof, the solid oral dosage according to the invention comprises as excipients microcrystalline cellulose in an amount of 35% to 45% by weight, hydroxypropylcellulose in an amount of 3.5 to 5.5% by weight, Mg stearate is present in an amount of 1.5 to 3.5% by weight, colloidal silicon dioxide is present in an amount of from 1.0% to 2.0% by weight, and talc is present in an amount of from 0.5 to 1.0% by weight, wherein the % by weight refers to the % by weight of the core prior to coating.

Further preferred amounts of LCZ696 and additives are shown in the illustrative examples.

The absolute amounts of each additive and the amounts relative to other additives is similarly dependent on the desired properties of the solid oral dosage form and may also be chosen by the skilled artisan by routine experimentation without undue burden. For example, the solid oral dosage form may be chosen to exhibit delayed release of the active agent with or without quantitative control of the release of active agent, especially in the presence of food added before patient administration.

Film Coating: The cores of the minitablet according to the present invention and as described herein are coated with a film-coating with a controlled release functionality and/or protective properties, wherein said coating may further serve to mask the taste of the drug substance and therefore improve patient compliance. In particular, the film-coating seves to control the release of the active ingredient, in particular LCZ696, in vitro and in vivo, especially aims to avoid dissolution already in foods added before use for more convenient drug administration.

In another embodiment, the dissolution rate behavior of the minitablets is aligned to that of the marketed mono tablets by modifying the release through application of the film coating.

Accordingly, in one embodiment of the invention, said film-coating prevents premature release of the drug when mixed with food.

In one embodiment of the invention, said film-coating having a controlled release functionality has a pH-dependent release profile, especially allowing to admix food known to the child (e.g. with a pleasant taste) before administration; in particular, the coating dissolves preferably only at a pH of 5 or lower, so that e.g. dissolution in food and thus, for example, loss of taste masking properties can be avoided. Or, in other words, the film coating is acid soluble up to a pH of 5.0.

In an embodiment thereof, the solid unit dosage form according to the invention has a film coating with a pH-dependent release profile leading to a similar or even slower in vitro dissolution of the active ingredient at a pH of 5.0 or lower in comparison to the in vitro dissolution of the active ingredient at a pH of 6.5 or above.

Accordingly, in one embodiment, the solid unit dosage form as described herein is provided, wherein said film-coating is adapted to lead to or leads to an in vitro dissolution of the active ingredient, in particular in the form of LCZ696, such that—when measured by the USP paddle method at about 50 rpm in 900 mL of 0.05M phosphate buffer at pH 6.8 and at 37±0.5° C.—after 10 min, an amount of about 30% (by weight) or more of valsartan and of about 25% (by weight) or more sacubitril are released, after 20 min, an amount of about 35% (by weight) or more of valsartan and of about 30% (by weight) or more sacubitril are released, and after 30 min, an amount of about 40% (by weight) or more of valsartan and of about 35% (by weight) or more sacubitril are released, wherein the % by weight refers to the % by weight of sacubtril and valsartan individually in relation to the weight of the total effective amount of the active ingredient sacubitril and valsartan in a 1:1 molar ratio.

In another embodiment thereof, the solid unit dosage form as described herein is provided, wherein said film-coating is adapted to lead to or leads to an in vitro dissolution of the active ingredient, in particular in the form of LCZ696, such that—when measured by the USP paddle method at about 50 rpm in 900 mL of 0.05M phosphate buffer at pH 6.8 and at 37±0.5° C.—after 10 min, an amount of about 35% (by weight) or more of valsartan and of about 30% (by weight) or more sacubitril are released, after 20 min, an amount of about 40% (by weight) or more of valsartan and of about 35% (by weight) or more sacubitril are released, and after 30 min, an amount of about 45% (by weight) or more of valsartan and of about 40% (by weight) or more sacubitril are released, wherein the % by weight refers to the % by weight of sacubtril and valsartan individually in relation to the weight of the total effective amount of the active ingredient sacubitril and valsartan in a 1:1 molar ratio.

In another embodiment, the solid unit dosage form as described herein is provided, wherein said film-coating is adapted to lead to or leads to an in vitro dissolution of valsartan so that
  at a pH of between about 2 and 4.5, particularly at a pH of 4.5, after 10 min of about 35% (by weight) or more, after 20 min of about 40% (by weight) or more, and after 30 min of about 45% (by weight) or more of valsartan is released, and/or
  at a pH of between about 6 and about 7, particularly at a pH of 6.8, after 10 min of about 40% (by weight) or less, after 20 min of about 45% (by weight) or less and after 30 min of about 50% (by weight) or less, of valsartan is released, wherein the % by weight refers to the % by weight of valsartan individually in relation to the weight of the total effective amount of the active ingredient sacubitril and valsartan in a 1:1 molar ratio.

In one embodiment, the test for measuring the dissolution of the individual active ingredient at neutral pH is performed following pharmacopeia USP <711> at pH 6.8 using a paddle method at 50 rpm and the dissolution medium is 900 mL of 0.05M phosphate buffer at pH 6.8 and at 37±0.5° C.

In one embodiment, the test for measuring the dissolution of the individual active ingredient at neutral pH is performed following pharmacopeia USP <711> at pH 4.5 using a paddle method at 50 rpm and the dissolution medium is 900 mL of 0.05M phosphate buffer at pH 4.5 and at 37±0.5° C.

In one embodiment, the test for measuring the dissolution of the individual active ingredient at acid pH is performed following pharmacopeia USP <711> at pH 2.0 using a paddle method at 50 rpm and the dissolution medium is 900 mL of 0.01 N HCl at pH 2.0 and at 37±0.5° C.

In one embodiment of the invention, the solid unit dosage form exhibits an in vitro dissolution profile of the active ingredient such that—when measured by the USP paddle method at about 50 rpm in 900 mL of 0.05M phosphate buffer at pH 6.8 and at 37±0.5° C.—the dissolution profile of a combined amount of minitablets equivalent to a 200 mg effective amount of active ingredient corresponds to the dissolution profile of the marketed 200 mg LCZ696 tablet formulation. Said release profile is disclosed within WO 2009/061713. In particular, an oral dosage form with a dosage of 200 mg of the therapeutic agent (sacubtril and valsartan in a 1:1 molar ratio) exhibits an in vitro dissolution profile, such that, when measured by the USP paddle method at about 50 rpm in 900 mL of 0.05M at pH 6.8 phosphate buffer and at 37±0.5° C., after 10 min, about 50% (by weight) or more of valsartan, is released, after 20 min, about 85% (by weight) or more of valsartan, is released, after 30 min, about 95% (by weight) or more of valsartan, is released, wherein here the % by weight refers to the % by weight of valsartan individually in relation to the weight of the effective amount of only the valsartan part of the active ingredient sacubitril and valsartan in a 1:1 molar ratio. I.e., since a 200 mg dose comprises 103 mg valsartan and 97 mg sacubitril, this corresponds to an in vitro dissolution profile, such that, when measured by the USP paddle method at about 50 rpm in 900 mL of 0.05M at pH 6.8 phosphate buffer and at 37±0.5° C., after 10 min, about 26% (by weight) or more of valsartan, is released, after 20 min, about 44% (by weight) or more of valsartan, is released, after 30 min, about 49% (by weight) or more of valsartan, is released, wherein the % by weight refers to the % by weight of sacubtril and valsartan individually in relation to the weight of the total effective amount of the active ingredient sacubitril and valsartan in a 1:1 molar ratio.

For the solid oral dosage forms in the form of film-coated minitablets according to the present invention the coating typically comprising a polymer like HPMC, PVP or the like, sugar, shellac or other film-coating entirely conventional in the art, and most preferably a polyacrylate. Attention is drawn to the numerous known methods of coating employed in the art, e.g., spray coating in a fluidized bed, e.g., by the known methods using apparatus available from Aeromatic, Glatt, Wurster or Hüttlin, in a perforated pan coater, e.g., by the known methods using apparatus from Accela Cota, Glatt, Driam or others, or other methods conventional in the art. The additives commonly used in confectioning may be employed in such methods.

In one embodiment, a solid unit dosage form according to the invention and as described herein is provided, wherein said film-coating comprises at least one polyacrylate as film forming agent.

In a preferred embodiment, the film-coating comprises a basic butylated methacrylate copolymer (optionally as defined in the European Pharmacopeia) as the film forming agent.

In another embodiment, a solid unit dosage form according to the invention and as described herein is provided, wherein said film-coat comprises an ammonium methacrylate copolymer, particularly an ammonium methacrylate copolymer type A (optionally as defined in the European Pharmacopeia) and/or an ammonium methacrylate copolymer Type B (optionally as defined in the European Pharmacopeia) as the film forming agent.

In one embodiment thereof, the polyacrylate is selected from
a) a basic butylated methacrylate copolymer formed from monomers selected from butyl methacrylate, (2-dimethylaminoethyl)methacrylate and methyl methacrylate, preferably a 1:2:1 copolymer formed from butyl methacrylate, (2-dimethylaminoethyl)-methacrylate and methyl methacrylate,
b) a copolymer formed from monomers selected from methacrylic acid and methacrylic acid lower alkyl esters; and
c) an ammonio methacrylate copolymer formed from monomers selected from ethyl acrylate, methyl methacrylate and trimethylammonioethyl methacrylate chloride.

In one particular variant the minitablets are coated with a polyacrylate, preferably an Eudragit$^R$ such as Eudragit$^R$-E or Eudragit®-RD100 or -RS/RL (see *Handbook of Pharmaceutical Excipients*, loc. cit. hereafter, p. 362), especially Eudragit®-E PO (Eudragit® is a trademark from Evonik Industries AG Kirschenallee, Darmstadt, Germany).

Accordingly, suitable coating materials for the compositions of the invention include polyacrylic polymers such as:
a) the 1:2:1 copolymer formed from butyl methacrylate, (2-dimethylaminoethyl)-methacrylate and methyl methacrylate available under the trademark Eudragit® E, especially Eudragit® E PO (chemical name: poly (butyl methacrylate-co-(2-dimethylaminoethyl) methacrylate-co-methyl methacrylate; CAS number: 24938-16-7) 1:2:1);
b) the 1:1 copolymers formed from monomers selected from methacrylic acid and methacrylic acid lower alkyl esters, such as the 1:1 copolymers formed from methacrylic acid and methyl methacrylate available under the trademark Eudragit® L, e.g. Eudragit® L100, and the 1:1 copolymer of methacrylic acid and acrylic acid ethyl ester available under the trademark Eudragit® L100-55;
c) the 1:2:0.2 copolymer formed from ethyl acrylate, methyl methacrylate and trimethylammonioethyl methacrylate chloride available under the trademark Eudragit® RL; or the corresponding 1:2:0.1 copolymer available under the trademark Eudragit® RS; or the 1:2:0.2 copolymer formed from ethyl acrylate, methyl methacrylate and trimethylammonioethyl methacrylate chloride which is in combination with carboxymethyl cellulose and available under the trademark Eudragit® RD;

more preferably those mentioned in a).

The polyacrylates above have preferably a mean molecular weight of about 30'000 to about 500'000, e.g. about 30'000 g/mol, respectively.

It has been found that polyacrylates, especially Eudragit® E PO, are particularly suitable for coating solid dosage forms comprising LCZ696 e.g. since a coating with Eudragit® E PO does not easily dissolve at the neutral pH of the mouth or any food it is to be administered with, but mainly at pH values below 5, and thereby prevents the dissolution of LCZ696 and ensure the complex stays intact until transfer to the stomach.

Coating materials as hereinabove defined may be used in admixture with further excipients conventional in coating formulations, for example talcum, magnesium stearate or stearic acid or silicon dioxide, for example synthetic amorphous silicic acid of the Syloid$^R$ type (Grace), for example Syloid$^R$ 244 FP, or colloidal silicon dioxide, e.g. Aerosil$^R$, e.g. Aerosil$^R$ 200, and/or wetting agents, for example sodium dodecyl sulfate (sodium lauryl sulphate), e.g. Duponol$^R$, or polyethyleneglycols or polysorbates.

Especially preferred compositions of the invention are accordingly coated LCZ696 comprising particles, e.g. tablets such as especially minitablets or pellets wherein the coating comprises a (taste-masking) polyacrylate coating, preferably Eudragit$^R$ E or Eudragit RD100®), especially Eudragit® E PO, and where in the coating, magnesium stearate or stearic acid is used/present as an anti-tack agent, basic butylated methacrylate copolymer as a film forming agent, sodium lauryl sulphate (Duponol) as a solubilizing agent and purified water as a solvent for coating (that is subsequently removed).

In one embodiment thereof, the solid dosage form of the present invention has a film coating which comprises in addition to the polyacrylate, in particular the basic butylated methacrylate copolymer, which preferably is an 1:2:1 copolymer formed from butyl methacrylate, (2-dimethylamino-ethyl)-methacrylate and methyl methacrylate, also sodium lauryl sulphate, stearic acid and talclum.

In one embodiment thereof, the coating comprises the basic butylated methacrylate copolymer in an amount of 50% to 70% by weight, preferably by 55% to 60% by weight, talcum in an amount of 20% to 40% by weight, preferably by 25% to 30% by weight, stearic acid or Mg stearat in an amount of 5% to 10% by weight, preferably by 7.5% to 9% by weight, sodium lauryl sulphate in an amount of 1% to 10% by weight, preferably by 4% to 8% by weight.

In another aspect the solid dosage forms may comprise a further coating, e.g. a layer of anti-sticking material applied upon one of the above-mentioned coatings, e.g. comprising a colloidal silicon dioxide product, e.g. Aerosil$^R$, which may avoid adhesion of the solid dosage forms to each other or to the walls of the container material, e.g. a capsule.

In one embodiment of the invention, the amount of the film coating of the solid dosage form may vary within a range of 0.1% to 10%, e.g. from 2.0 to 8.5% by weight of the total dosage form including core and coating. A preferred amount of the film coating ranges from about 4% to about 8% by weight, representing, for example, about 0.2 mg to 0.4 mg per 7 mg minitablet unit.

In another embodiment, the amount of film coating may vary within a range of 0.1 to 5 mg/cm2, e.g. 0.4 mg/cm$^2$ to 0.7 mg/cm$^2$.

Process: For the preparation of the core tablet comprising a therapeutically effective amount of sacubitril and valsartan in a 1:1 molar ratio, in particular in the form of LCZ696, dry granulation, especially roller compaction, may preferably be used. Wet granulation may lead to a change of the drug substance and may cause stability issues.

Dry granulation of LCZ696 using a mixture of dry drugs substance and excipients has been found to be the best way of manufacturing suitable LCZ696 solid oral dosage forms according to the invention, especially minitablets, showing following advantages:
The influences of a changing drug substance quality are minimized;
A robust manufacturing process of the DP is achieved;
Scale-up of formulation and process resulting in a reproducible DP performance is achieved; and
appropriate stability to achieve a reasonable shelf life is achieved.

The excipients may be distributed partly in an inner (granular) phase and partly in an outer phase of the core, which preferably is the case in the described invention. Preferably, the filler, especially microcrystalline cellulose, a glidant, especially colloidal silicone dioxide and a lubricant, especially Mg stearate, are partly in the inner and partly in the outer phase; a binder, especially hydroxypropyl cellulose, being the binder during granulation, and a further glidant, especially talc, are only part of the inner phase; and only filler, especially microcrystalline cellulose, glidant, especially colloidal silicon dioxide and lubricant, especially Mg stearate, are present in the outer phase.

The inner phase excipients, e.g., filler, glidant(s), binder and lubricant, and the drug substance are mixed and granulated using roller compaction. The granulate is sieved. The outer phase containing, e.g., filler, glidant and lubricant, is screened with the granulate and mixed. The mixture is compressed into minitablets. The cores are preferably coated with a film-coat.

The granulate phase is defined as the inner phase, the excipients added to the granulate are defined as the outer phase of the tabletting mixture.

The invention likewise relates to a process for the preparation of solid oral dosage forms as described herein above and below. Such solid oral dosage form may be produced by working up components as defined herein above in the appropriate amounts, to form unit dosage forms according to the invention, especially minitablets.

Accordingly, the present invention provides a process for the manufacture of a solid oral dosage form of the present invention comprising:
a) mixing the active ingredient and additives of the inner phase and dry granulating (especially roller compacting) said components; optionally using intervening screening steps;
b) mixing the granulate with outer phase excipients;
c) compressing a resulting mixture to form a solid oral dosage as a core (especially a mini-) tablet core), preferably using a multiple tip tooling; and
d) coating a resulting core tablet to give a film-coated tablet, especially minitablet.

Preferably, the additives in step (a) are selected from a filler, at least one glidant, a lubricant and a binder; and the outer phase excipients in step (b) are selected from a filler, a lubricant and a glidant.

The manufacturing of the granulate can be performed on standard equipment suitable for granulation processes. The manufacturing of the final blend and the compression of tablets can also be performed on standard equipment.

For example, in step (a) the blending may be carried out by a diffusion mixer (tumble) or bin blender, e.g. a Bohle container blender or Turbula T10B, a first screening may be performed with a screening mill, e.g. with 0.8 mm round wire/oscillating bar, e.g. a Frewitt, the granulation may take place using a roller compactor, e.g. Bepex 200/50, resulting in granulated material, followed by another screening step e.g. as just described but replacing the 0.8 mm round wire with 1.0 mm round wire. Then step (b) may be conducted by blending in filler and glidant with a diffusion mixer (tumble) or bin blender, e.g. using a Turbula T10B or Bohle container blender, followed by screening e,g, with a hand sieve, 0.8 mm, adding (after screening it e.g. with a 0.8 mm hand sieve) further lubricant and blending with a diffusion mixer (tumble) or bin blender, e.g. a Turbula T10B or Bohle container blender. Then step (c) may be carried out using a dry compression method, e.g., tablet press, such as a Korsch PH250, Korsch XL400or Fette P1200i. This results in cores.

Minitablets are compressed on a standard rotary tablet press with special multi-tip tooling. Multi-tip tooling can e.g. consist of up to 19 tips per punch. Such minitablet punches have a larger contact area in the die compared with a standard tablet punch. Therefore the particle size distribution and the powder flow properties are important to obtain unifom tablet mass. The lubrication of the formulation and/or tooling (e.g. spray lubrication) options play an advantageous role in the manufacturing process.

As described above, the core tablets are then, in a step (d), be film-coated to provide a film-coated (especially mini-) tablet as described herein before. The coating mixture may, for example, be prepared by mixing the ingredients, including water, using a stirrer, e.g. from IKA with screw-stirrer, followed by screening, e.g. with a hand sieve, 0.5 mm, and subsequent coating of the cores obtained in step (c), e.g. using a fluidized bed dryer with e.g. direct heating, such as an Aeromatic-Fielder MP1 with Wurster fixation using an (e.g. Watson Marlow) peristaltic pump and tubings of suitable diameter Due to the high water solubility of LCZ696, prolonged contact with water has preferably to be avoided in order to prevent the drug substance from decomposition. The coating process typically removes the water instantaneously thus preventing prolonged contact with LCZ696. Alternatively, applying an organic film-coating process may provide a way to avoid negative impact on the complex.

In order to overcome the adverse concurrence of high surface area of minitablets coupled with the slight hygroscopicity of LCZ696 and the issues associated therewith, the drying conditions in the pan may be modified in order to reduce the high water content in the film-coated minitablets. This may be achieved by using a coating instrument with improved drying conditions such as, for example, a fluidized bed coater.

The coating may also comprise pigments, e.g. iron oxide pigments, titanium dioxide as coloring agent(s), or one or more dyes may serve to enhance the appearance as well as to identify the compositions. Dyes suitable for use typically include but are not limited to carotinoids, chlorophyll and lakes.

Use: The solid oral dosage forms of the present invention can be used in pediatrics for treating or preventing (together "treatment of") cardiovascular or renal diseases, in particular heart failure, or in the manufacture of a medicament for treating or preventing (together "treatment of") cardiovascular or renal diseases, in particular heart failure.

The present invention likewise relates to a method of treating (including prophylactic treatment) cardiovascular or renal diseases, in particular heart failure, comprising administering to children, particularly to children of 0.5-17 years of age, in need of such treatment a therapeutically effective solid oral dosage form according to the present invention.

The present invention likewise relates to the use of a solid oral dosage form according to the present invention for the manufacture of a medicament for the pediatric treatment (the term "treatment" including prophylactic treatment) of cardiovascular or renal diseases, in particular heart failure.

The present invention likewise relates to a pharmaceutical composition for the pediatric treatment (the term "treatment" including prophylactic treatment) of cardiovascular or renal diseases, in particular heart failure, comprising a solid oral dosage form according to the present invention.

Ultimately, the exact dose of the active agent and the particular formulation to be administered depend on a number of factors, e.g., the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect. The minitablets allow for simple adaptation of the dosage by simply varying the number of minitablets used for administration in accordance with (especially individual) patient requirements.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not as limitation of the scope of the present invention.

EXAMPLES

Study Drug: LCZ696:

LCZ696 refers to the supramolecular complex trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate. This compound and pharmaceutical compositions thereof have been previously disclosed in WO2007/056546 and WO 2009/061713, whose preparative teachings are incorporated herein by reference.

Example 1: Preparation of Minitablets

Batches of 200,000 up to 1,303,142 dosage unit forms (film coated minitablets of size 2.0 mm, round curved) were manufactured, where each unit dosage form has the following composition and contains an effective amount of 3.125 mg of sacubitril and valsartan in a 1:1 molar ratio (corresponding to 3.534 mg LCZ696 or a theoretical amount of 3.368 mg LCZ696 anhydrous acid, i.e. sacubitril, valsartan and sodium, but without the water):

Excipients:
Cellulose MK GR is microcrystalline cellulose from e.g. JRS Pharama, Germany (Vivapur 102)
HP cellulose 300-600 CPS is hydroxypropyl cellulose from e.g. Ashland Specialty, South Park, US
Aerosil® 200 is colloidal silica (fumed silica) Evonik, Germany.
Duponol® is sodium lauryl sulphate from e.g. tensa Chem, Belgium.
Basic polymethacrylate E PO refers to Eudragit® E PO, Evonik Germany The composition of the the minitablet is described in below table 1:

TABLE 1

| Component | Ingredient | Composition per unit [mg/unit] |
|---|---|---|
| Outer phase (granulate) | LCZ696 | 3.534[1] |
| | Cellulose MK GR[3] | 2.121 |
| | HP cellulose 300-600 CPS | 0.312 |
| | Aerosil 200 | 0.031 |
| | Talcum | 0.047 |
| | Magnesium stearate | 0.094 |
| Complete Granulate weight | | 6.139 |
| Inner Phase | Cellulose MK GR | 0.686 |
| | Aerosil 200 | 0.070 |
| | Magnesium stearate | 0.105 |

TABLE 1-continued

| Component | Ingredient | Composition per unit [mg/unit] |
|---|---|---|
| Resulting core weight | | 7.000 |
| Coating | Duponol | 0.0171 |
| | Basic polymethacrylate EPO | 0.1713 |
| | Stearic acid | 0.0258 |
| | Talcum | 0.0856 |
| | Water purified[2] | — |
| Final Coated Tablet Weight | | 7.2998 |

[1]salt & hydrate factor 1.131 (ratio of sum of valsartan, sacubitril plus sodium and crystal water to molecular weight of valsartan plus sacubitril without sodium and without crystal water); that is, the 3.534 mg correspond to 3.125 mg of pure valsartan plus pure sacubitril.
[2]removed during processing
[3]designated excipient to compensate for an adjusted weight of the drug substance, if the content is <99.5 weight percent.

Manufacturing Process:

Step 1: LCZ696, Cellulose MK-GR, Aerosil, HP cellulose 300-600 CPS, Mg stearate and talcum are subjected to blending at 150 revolutions, yielding a mixture.

Step 2: The resulting mixture is subjected to a screening step, yielding PREMIX I.

Step 3: PREMIX I is subjected to mixing at 100 revolutions, yielding PREMIX II.

Step 4: PREMIX II is subjected to Dry granulation (Roller compacting).

Step 5: The resulting granules are subjected to Screening at 1.0 mm.

Step 6: Cellulose MK GR and Aerosil for the outer phase are subjected to screening 0.8 mm and added in Step 7 to the granules and then blended at 100 revolutions.

Step 8: Mg stearate for the outer phase is subjected to screening at 0.8 mm and added to the blend obtained after Step 7.

Step 9: The mixture from Step 8 is subjected to a blending at 60 revolutions, yielding the FINAL BLEND (for the tablet core).

Step 10: The FINAL BLEND is subjected to tabletting, resulting in the bulk core material.

The following tableting tools are used:

| Punch | Punch design |
|---|---|
| Upper | Round curved, with 19 single punch tips per punch (EPMO/Elisabeth punches*) |
| Lower | Round curved, with 19 single punch tips per punch (EPMO/Elisabeth punches*) |

*)Elizabeth, McKeesport, Pennsylvania, US

Step 11: Basic polymethacrylate E PO, stearic acid, Duponol and purified water are mixed at 700 revolutions.

Step 12: To the mixture of Step 11, talcum is added and the material is mixed.

Step 13: The resulting blend from Step 12 is subjected to screening, resulting in the film coating suspension which is applied by spray coating onto the bulk core material from Step 10 in a fluidized bed under direct heating (for example, a product temperature during coating of 28-35° C. using 1.2 mm nozzle a spray rate 4-8 g/min, spray pressure 1.5 bar for a 500 g batch size).

"Revolutions" refers to rotations per minute.

Manufacturing Equipment:

| Process Step | Equipment type | Manufacturer, model, size |
|---|---|---|
| 1 Blending | Diffusion mixer (tumble), bin blender | Bohle container blender or Turbula |
| 2 Screening | Screening mill, 0.8 mm round wire, oscillating bar | Frewitt |
| 3 Blending | Diffusion mixer (tumble), bin blender | Turbula T10B or Bohle container blender |
| 4 Dry granulation | Roller compactor | Bepex 200/50; Bepex 200/30 |
| 5 Screening | Screening mill, 1.0 mm round wire, oscillating bar | Frewitt |
| 6 Screening | Hand sieve, 0.8 mm | Hand sieve, 0.8 mm |
| 7 Blending | Diffusion mixer (tumble), Bin blender | Turbula T10B or Bohle container blender |
| 8 Screening | Hand sieve, 0.8 mm | Hand sieve, 0.8 mm |
| 9 Final Blending | Diffusion mixer (tumble), Bin blender | Turbula T10B or Bohle container blender |
| 10 Tabletting | Tablet press, power assisted | Korsch PH250 or Fette P1200i |
| 11, 12 Coating mixture preparation | Stirrer | IKA with screw-stirrer |
| 13 Screening and Film coating | Hand sieve, 0.5 mm | Hand sieve, 0.5 mm |
| | Direct heating, fluidized solid beds (Fluidized bed dryer) | Aeromatic-Fielder MP1 with Wurster Watson Marlow |
| | Peristaltic pump | ID: 1.6 mm, OD: 4.8 mm |
| | Tubings | ID: 3.2 mm; OD 6.4 mm |

The resulting tablets are packaged as sub-batches in flat pouches from PETP/Al/PE.

Example 2: Minitablet Dosage Form

Minitablets are filled in a bottle of 64 count (total content 200 mg), or they are provided in capsules, each containing either 4 minitablets (12.5 mg total), or 10 minitablets (31.25 mg total). These have been created to make it easier for subjects/parents/guardians, as well as pharmacy staff to dispense the correct dose.

Example 3: Dissolution Testing

The tablets of the Examples are tested for their dissolution in 900 ml of pH 6.8 phosphate buffer with paddles at 50 rpm.

The assembly consists of the following: a covered vessel made of glass or other inert, transparent material; a motor, and a paddle formed from a blade and shaft as the stirring element. The vessel is partially immersed in a suitable water bath of any convenient size or placed in a heating jacket. The water bath or heating jacket permits holding the temperature inside the vessels at 37±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is has the following dimensions and capacities: the height is 160 mm to 210 mm and its inside diameter is 98 mm to 106 mm. Its sides are flanged at the top. A fitted cover may be used to retard evaporation. The shaft is positioned so that its axis is not more than 2 mm at any point from the vertical axis of the vessel and rotates smoothly without significant wobble. The vertical center line of the blade passes through the axis of the shaft so that the bottom of the blade is flush with the bottom of the shaft. The design of the paddle is as shown in USP <711>, FIG. 2. The distance of 25±2 mm between the blade and the inside bottom of the vessel is maintained during the test. The metallic or suitably inert, rigid blade and shaft comprise a single entity. A suitable two-part detachable design may be used provided the assembly remains firmly engaged during the test. The paddle blade and shaft may be coated with a suitable inert coating. The dosage unit or the combined amount of dosage units is allowed to sink to the bottom of the vessel before rotation of the blade is started. A small, loose piece of nonreactive material such as not more than a few turns of wire helix may be attached to dosage units that would otherwise float. Other validated sinker devices may be used.

900 mL of a buffered aqueous solution, adjusted to pH 6.8±0.05 (0.05 M Phosphate buffer solution obtained by dissolving 6.805 g of potassium dihydrogen phosphate and 0.896 g of sodium hydroxide in and diluting to 1000 ml with water, and adjusting the pH to 6.80±0.05 using 0.2M sodium hydroxide or 1M phosphoric acid; referred hereinafter as "Dissolution Medium") is placed in the vessel of the apparatus, the apparatus is assembled, the Dissolution Medium is equilibrated to 37±0.5°, and the thermometer is removed. 1 dosage form (e.g. tablet or capsule) is placed on the apparatus, taking care to exclude air bubbles from the surface of the dosage-form unit, and immediately the apparatus is operated at a rate of 50+2 rpm. Within the time interval specified (e.g. 10, 20, 30, 45, 60, 90 and 120 min.), or at each of the times stated, a specimen(>1 ml) is withdrawn from a zone midway between the surface of the Dissolution Medium and the top of the rotating blade, not less than 1 cm from the vessel wall. [NOTE—the aliquots withdrawn for analysis are replaced with equal volumes of fresh Dissolution Mediums at 37° or, where it can be shown that replacement of the medium is not necessary, the volume change is corrected in the calculation. The vessel is kept covered for the duration of the test, and the temperature of the mixture under test at suitable times is verified.].

The specimen is filtered through a suitable filter, e.g. a 0.45 μm PVDF filter (Millipore) and the first mls (2 to 3 ml) of the filtrate are discarded. The analysis is performed by HPLC or UV detection. The test is repeated at least 6 times. with additional dosage form units.

The tablets of the Examples can also be tested using the above method at pH 4.5 by carrying out the method as described above and optionally applying the following modifications: Preparation of pH 4.5 phosphate buffer solution is achieved by dissolving 13.61 g of potassium dihydrogen phosphate in 750 ml of water, adjusting the pH if necessary with 0.1M sodium hydroxide or with 0.1M hydrochoric acid and diluting to 1000.0 ml with water.

Alternative dissolution testing condition at pH 4.5:

Speed of rotation 75±3 rpm; Test medium 900 mL of Phosphate buffer solution pH 4.5.

Reference Example:200 mgLCZ696 tablets

The following Table 2 shows the formulation for 100, 200 and 400 mg effective amount of therapeutic agent (taken from WO 2009/061713, page 18 ff and adapted).

TABLE 2

| Ingredients | 100 mg mg/Tablet | 200 mg mg/Tablet | 400 mg mg/Tablet |
|---|---|---|---|
| INTRAGRANULAR | | | |
| LCZ696 | 113.1 | 226.2 | 452.4 |
| Corresponds to LCZ696 (anhydrous free acid) | 107.8 | 215.6 | 431.2 |
| Microcrystalline Cellulose (Cellulose MK GR) | 34.9 | 69.8 | 139.6 |
| L-HPC (low sub) | 25.0 | 50.0 | 100.0 |
| Crospovidone | 10.0 | 20.0 | 40.0 |
| Colloidal silicon dioxide | 1.0 | 2.0 | 4.0 |
| Talc | 1.5 | 3.0 | 6.0 |
| Magnesium Stearate | 3.0 | 6.0 | 12.0 |
| EXTRAGRANULAR | | | |
| Talc | 0.5 | 1.0 | 2.0 |
| Crospovidone | 8.0 | 16.0 | 32.0 |
| Magnesium Stearate | 3.0 | 6.0 | 12.0 |
| COATING | | | |
| Opadry White | 4.43 | 6.63 | 9.95 |
| Opadry Yellow | 2.86 | 4.30 | 6.44 |
| Opadry Red | 0.65 | 0.98 | 1.47 |
| Opadry Black | 0.06 | 0.09 | 0.14 |
| Weight gain per tablet (mg) | 8 | 12 | 18 |
| Total Tablet weight (mg) | 208 | 412 | 818 |

The manufacturing process is as described in WO 2009/061713, page 20.

Example 5: Comparison of Bioavailability

Purpose: The purpose of this study was to determine the relative bioavailability of 200 mg of LCZ696 mini-tablets compared to the 200 mg LCZ696 final market image tablet under fasted conditions and also to evaluate the effect of food on the bioavailability of 200 mg LCZ696 mini-tablets. To evaluate food effect LCZ696, mini- tablets were administered with a table-spoonful of pudding or with pudding and a high fat meal.

Study Design: A randomized, open-label, single dose, crossover study in healthy subjects. Enrolled: 40; completed: 39 subjects.

Treatment A: single oral dose of LCZ696 200 mg FMI

Treatment B: single oral dose of LCZ696 200 mg of LCZ696 mini-tablets

Treatment C: single oral dose of LCZ696 200 mg of LCZ696 mini-tablets sprinkled on a tablespoon of pudding Treatment D: single oral dose of LCZ696 200 mg of LCZ696 mini-tablets sprinkled on a tablespoon of pudding and administered with a high fat meal Pharmacokinetics: The statistical analysis of relative bioavailability of mini-tablets compared to FMI tablets, effect of pudding, and effect of high fat meal are presented in Table 4.

Following oral administration of the single oral 200 mg dose under fasting conditions, the primary PK parameter variables of sacubitril, LBQ657, and valsartan were similar between mini-tablets and FMI tablet as geometric mean ratio and corresponding 90% CI for both $C_{max}$ and AUC were within 80-125%. The $T_{max}$ values were also similar between these two formulations suggesting no impact of formulation effect on rate of absorption.

Similarly, when 200 mg of mini-tablets were administered with a table spoonful of vanilla pudding, the GMR and the 90% Cl for $AUC_{last}$, $AUC_{inf}$ and $C_{max}$ for LCZ696 were also within 0.80-1.25 range, indicating no significant effect of a small amount of vanilla pudding on the bioavailability of mini-tablets. The Tmax values were also similar between these two treatments suggesting no impact of vanilla pudding on rate of absorption of LCZ696 analytes.

When a single dose of LCZ696 200 mg mini-tablets sprinkled on pudding was administered with a high fat meal, the $C_{max}$, of sacubitril and LBQ657 was decreased by 60% and 19%, respectively. However, the $AUC_{inf}$ and $AUC_{last}$ of sacubitril and LBQ657 were not affected by high fat food as the GMR and 90% Cl were within 80-125% range. Food delayed the absorption of sacubitril and LBQ657 from mini-tablets by 2.5 hrs and 2 hrs, respectively. When LCZ696 mini-tablets were administered with a high fat meal, the Cmax and AUC of valsartan decreased by 57% and 41%, respectively. The rate of absorption of valsartan was also delayed by 2 hrs when LCZ696 mini-tablets were administered with food.

The relative bioavailability of LCZ696 analytes following administration of 200 mg mini-tablets compared to 200 mg FMI tablets and the effect of pudding and of a high fat meal on PK exposure with mini-tablets are presented in Table 3.

TABLE 3

Assessment of relative bioavailability of LCZ696 analytes following administration of 200 mg of mini tablets compared to 200 mg FMI tablets and effect of pudding and high fat meal on PK exposure with mini tablets

| | PK Parameter | Mini tablets vs FMI tablet[a] (Fasting) | Pudding vs fasting[b] (Mini tablets) | Pudding + High fat meal vs Pudding[c] (Mini tablets) |
|---|---|---|---|---|
| Sacubitril | AUCinf (ng · h/ml) | 0.96 (0.92-1.00) | 1.04 (1.00-1.08) | 1.01 (0.97-1.05) |
| | AUClast (ng · h/ml) | 0.96 (0.92-1.00) | 1.04 (1.00-1.08) | 1.00 (0.96-1.04) |
| | Cmax (ng/ml) | 0.94 (0.8-1.11) | 1.00 (0.85-1.18) | 0.4 (0.34-0.46) |
| LBQ657 | AUCinf (ng · h/ml) | 0.98 (0.96-0.99) | 1.01 (0.99-1.03) | 1.02 (1.00-1.04) |
| | AUClast (ng · h/ml) | 0.98 (0.96-0.99) | 1.01 (0.99-1.03) | 1.02 (1.00-1.04) |
| | Cmax (ng/ml) | 0.95 (0.91-0.99) | 0.99 (0.95-1.03) | 0.81 (0.77-0.85) |
| Valsartan | AUCinf (ng · h/ml) | 1.11 (1.00-1.24) | 1.02 (0.93-1.11) | 0.6 (0.54-0.66) |
| | AUClast (ng · h/ml) | 1.11 (1.00-1.22) | 1.04 (0.94-1.14) | 0.59 (0.54-0.65) |
| | Cmax (ng/ml) | 1.09 (0.98-1.21) | 1.02 (0.92-1.13) | 0.43 (0.38-0.48) |

Data is presented as geometric mean ratio (90% CI) for:
[a]test (minitablets)/reference (FMI tablet)
[b]test (minitablets with pudding)/reference (Minitablets)
[c]test (minitablets on pudding + high fat meal)/reference (minitablets with pudding)

CONCLUSIONS

The rate (Cmax) and extent (AUC) of absorption of LCZ696 analytes were comparable between LCZ696 200 mg of mini-tablets and LCZ696 200 mg FMI tablet in healthy subjects under fasted condition.

The rate (Cmax) and extent (AUC) of absorption of LCZ696 analytes were comparable when LCZ696 200 mg of mini-tablets were administered with or without a small amount of vanilla pudding.

When LCZ696 200 mg of LCZ696 mini-tablets sprinkled on pudding was administered with a high fat meal, the Cmax of AHU377, LBQ657, and valsartan decreased by 60%, 19%, and 57%, respectively. However, the extent of absorption (AUCs) of AHU377 and LBQ657 was comparable while the extent of absorption (AUCs) of valsartan was reduced by ~40%.

The invention claimed is:

1. A minitablet for oral administration having a core and an outer coating and having a diameter of 1 mm to 4 mm, wherein the core comprises:
   an amount of sacubitril and valsartan in a 1:1 molar ratio as an active ingredient; and
   at least one pharmaceutically acceptable excipient,
   wherein the amount is about 2 mg to about 5 mg, corresponding to a respective combined amount of valsartan (free acid) and sacubitril (free acid) in a 1:1 molar ratio,
   wherein the outer coating is in a form of a controlled release and/or a protective film-coating, and
   wherein the film-coating has a basic butylated methacrylate copolymer content of 50% to 70% by weight of the film coating.

2. The minitablet according to claim 1, wherein the core comprises trisodium [3-((1S,3R)-1-biphenyl-4-ylmethyl-3-ethoxycarbonyl-1 -butylcarbamoyl)propionate-(S)-3'-methyl-2'-(pentanoyl{2"-(tetrazol-5-ylate) biphenyl-4'-ylmethyl}amino)butyrate] hemipentahydrate as the active ingredient.

3. The minitablet according to claim 1, wherein the diameter of the minitablet is 1 mm to 3 mm.

4. The minitablet according to claim 1, wherein the minitablet contains 3.125 mg of the active ingredient.

5. The minitablet according to claim 1, wherein the mini-tablet contains about 3 mg to about 4 mg of trisodium [3-((1S,3R)-1-biphenyl-4-ylmethyl-3-ethoxycarbonyl-1 -butylcarbamoyl)propionate-(S)-3'-methyl-2'-(pentanoyl{2"-(tetrazol-5-ylate) biphenyl-4'-ylmethyl}amino) butyrate] hemipentahydrate.

6. The minitablet according to claim 1, wherein the film-coating comprises a basic butylated methacrylate copolymer formed from monomers selected from butyl methacrylate, (2-dimethylaminoethyl)methacrylate, and methyl methacrylate.

7. The minitablet according to claim 6, wherein the basic butylated methacrylate copolymer is a 1:2:1 copolymer formed from butyl methacrylate, (2-dimethylaminoethyl)-methacrylate and methyl methacrylate.

8. The minitablet according to claim 1, wherein the film-coating further comprises sodium lauryl sulphate, stearic acid, and talcum.

9. The minitablet according to claim 1, wherein the film-coating further comprises talcum at a content of 20% to 40% by weight of the film-coating, stearic acid or magnesium stearate at a content of 5% to 10% by weight of the film-coating, and sodium lauryl sulphate at a content of 4% to 8% by weight of the film-coating.

10. The minitablet according to claim 1, wherein a weight of the film-coating is about 4% to about 8% based on a total weight of the minitablet.

11. The minitablet according to claim 1, wherein a content of the active ingredient in the core is 30% to 70% by weight.

12. The minitablet according to claim 1, wherein the at least one pharmaceutically acceptable excipient comprises (i) microcrystalline cellulose, (ii) hydroxypropylcellulose, (iii) magnesium, calcium, or aluminum stearate, (iv) anhydrous colloidal silica (colloidal silicon dioxide), and (v) talc.

13. The minitablet according to claim 12, wherein microcrystalline cellulose is present in an amount of 35% to 45% by weight, hydroxypropylcellulose is present in an amount of 2% to 8% by weight, magnesium stearate is present in an amount of 1.0 to 5.0% by weight, colloidal silicon dioxide is present in an amount of from 1.0% to 2.0% by weight, and talc is present in an amount of from 0.5 to 1.0% by weight, wherein the % by weight refers to the % by weight of the core.

14. A combination of minitablets and a dispenser, wherein the minitablets comprise the minitablet according to claim 1.

15. A capsule containing 1, 2, 3, 4, 5, 6, 7, 8, 9, 10, 11, 12, 13, 14, 15, 16, 17, 18, 19, or 20 minitablets, wherein the minitablets comprise the minitablet according to claim 1.

16. A method of treating heart failure in a pediatric patient, comprising administering to the pediatric patient in need of such treatment the minitablet according to claim 1.

17. A method of treating chronic heart failure, hypertension, angina, myocardial infarction, atherosclerosis, diabetic nephropathy, diabetic cardiac myopathy, renal insufficiency, peripheral vascular disease, left ventricular hypertrophy, cognitive dysfunction or stroke in a patient where low and individual dosing is required or who encounter problems with swallowing, comprising administering to the patient the minitablet according to claim 1.

18. The minitablet according to claim 1, wherein the film-coating dissolves only at a pH of 5 or lower.

* * * * *